US009457094B2

(12) United States Patent
Kim et al.

(10) Patent No.: US 9,457,094 B2
(45) Date of Patent: Oct. 4, 2016

(54) PHARMACEUTICAL COMPOSITION CONTAINING FIMASARTAN AND HYDROCHLOROTHIAZIDE

(71) Applicant: Boryung Pharmaceutical Co., Ltd., Seoul (KR)

(72) Inventors: Je Hak Kim, Anyang-si (KR); Kyung Wan Nam, Gunpo-si (KR); Seo Hun Park, Suwon-si (KR); Ju Won Kim, Seoul (KR); Sang Yeop Kim, Ansan-si (KR)

(73) Assignee: Boryung Pharmaceutical Co., Ltd., Seoul (KR)

( * ) Notice: Subject to any disclaimer, the term of this patent is extended or adjusted under 35 U.S.C. 154(b) by 70 days.

(21) Appl. No.: 14/411,871

(22) PCT Filed: Apr. 30, 2013

(86) PCT No.: PCT/KR2013/003734
§ 371 (c)(1),
(2) Date: Dec. 29, 2014

(87) PCT Pub. No.: WO2014/003305
PCT Pub. Date: Jan. 3, 2014

(65) Prior Publication Data
US 2015/0147394 A1 May 28, 2015

(30) Foreign Application Priority Data
Jun. 28, 2012 (KR) .................. 10-2012-0070359

(51) Int. Cl.
*A61K 47/38* (2006.01)
*A61K 9/20* (2006.01)
*A61K 31/506* (2006.01)
*A61K 47/32* (2006.01)
*A61K 31/549* (2006.01)
*A61K 31/513* (2006.01)

(52) U.S. Cl.
CPC ............... *A61K 47/38* (2013.01); *A61K 9/20* (2013.01); *A61K 9/2018* (2013.01); *A61K 9/2027* (2013.01); *A61K 9/2054* (2013.01); *A61K 9/2095* (2013.01); *A61K 31/506* (2013.01); *A61K 31/513* (2013.01); *A61K 31/549* (2013.01); *A61K 47/32* (2013.01)

(58) Field of Classification Search
None
See application file for complete search history.

(56) References Cited

U.S. PATENT DOCUMENTS

| 2005/0089575 A1 | 4/2005 | Friedl et al. |
| 2010/0247649 A1 | 9/2010 | Palaparthi et al. |
| 2014/0134247 A1 | 5/2014 | Beso et al. |

FOREIGN PATENT DOCUMENTS

| CN | 102397278 A | 4/2012 |
| CN | 102485227 A | 6/2012 |
| CN | 102485228 A | 6/2012 |
| KR | 10-2004-0079937 A | 9/2004 |
| KR | 10-0678421 B1 | 2/2007 |
| WO | WO 2006/112596 A1 | 10/2006 |
| WO | WO 2007/144175 A2 | 12/2007 |
| WO | WO 2009/058950 A2 | 5/2009 |
| WO | WO 2011/060945 A2 | 5/2011 |

OTHER PUBLICATIONS

ClinicalTrials.gov, A Clinical Study to Evaluate Efficacy and Safety of Fimasartan/Hydrochlorothiazide Combination-therapy, Jan. 2012, ClinicalTrials.gov, 4 pages.*
Jeon, H., et al., "Assessment of the Drug-Drug Interactions Between Filmasartan and Hydrochlorothiazide in Healthy Volunteers," *Journal of Cardiovascular Pharmacology* 59(1):84-91, Raven Press, United States (2012).
English Translation of The International Search Report for International Application No. PCT/KR2013/003734, Korean International Property Office, Republic of Korea, mailed on Aug. 29, 2013.
"Tablet Manufacture," in *Encyclopedia of Pharmaceutical Technology*, $3^{rd}$ Edition, vol. 6, Swarbrick, J., ed., pp. 3657-3658, Informa Healthcare USA, Inc., United States (2007).
Extended European Search Report and Search Opinion for EP Application No. 13809531.0, European Patent Office, Germany, mailed on Jan. 15, 2016, 9 pages.
Handbook of Pharmaceutical Excipients, 5th edition, eds. Rowe, R.C., et al., pp. 336-343, 346-349, and 611-616, Pharmaceutical Press, England (2006).
Otsuka, A. et al., Funtai wo chu-shin to shita seizaigaku (pharmaceutics focusing on powders), 4th Edition, pp. 164-168, Hirokawa Publishing Co., Japan (1976).
Ikuo, S., "ARB/Diuretic Complex and Drug Compliance," *Journal of Blood Pressure* 13(12): 1354-1357, Japan (2006).
Tuda, K. et al., Pharmaceutical Engineering, First Edition, pp. 161-163, Japan (1971).
Mitsuo, H., "Expectation for ARB/diuretic complex based on evidence," *Journal of Blood Pressure* 13(12): 1349-1353, Japan (2006).
Okano, S., Introduction to Modern Pharmaceutics, Revised 3rd Edition, pp. 138-140, Japan (1987).
Takuya, T., "Development of complex comprising antihypertensive diuretics and future directivity," *Journal of Blood Pressure* 13(1):65-69, Japan (2006).

* cited by examiner

*Primary Examiner* — Trevor Love
(74) *Attorney, Agent, or Firm* — Sterne, Kessler, Goldstein & Fox P.L.L.C.

(57) ABSTRACT

The present invention provides: a pharmaceutical composition having a superior physical property since fimasartan and hydrochlorothiazide, which are main components of a combination preparation, have superior content uniformity; and a preparation method thereof.

18 Claims, No rawings

PHARMACEUTICAL COMPOSITION CONTAINING FIMASARTAN AND HYDROCHLOROTHIAZIDE

TECHNICAL FIELD

The present invention relates to a pharmaceutical composition comprising fimasartan and hydrochlorothiazide and, more particularly, to a pharmaceutical composition comprising fimasartan, an angiotensin II receptor antagonist, and hydrochlorothiazide, a diuretic.

BACKGROUND ART

Fimasartan is known as an angiotensin II receptor antagonist developed for the treatment of hypertension and other medical indications (Korean Patent No. 10-1058284), Fimasartan is chemically defined as 2-n-butyl-5-dimethyl-aminothiocarbonylmethyl-6-methyl-3-[[2'-(1H-tetrazol-5-yl)biphenyl-4-yl]methyl]pyrimidin-4(3H)-one, is a nonpeptide molecular-chemically defined, and has an empirical formula of $C_{27}H_{30}N_7OS$ and a molecular weight of 501.65. Fimasartan has been approved as a pharmaceutical product, fimasartan potassium trihydrate, for use in South Korea and commercially available.

Moreover, hydrochlorothiazide is a diuretic that is orally administered for the treatment of edema and hypertension and has a chemical name of 6-chloro-3,4-dihydro-2H-1,2,4-benzothiadiazine-7-sulfonamide-1,1-dioxide, an empirical formula of $C_7H_8ClN_3O_4S_2$, and a molecular weight of 297.74.

The combination therapy with an ARB drug including fimasartan, and hydrochlorothiazide as a diuretic, has been known to exhibit synergistic therapeutic efficacy in the treatment of hypertension, and thus many studies have been conducted to structurally combine the ARB drug and the diuretic hydrochlorothiazide, but it is difficult to uniformly combine two drugs in pharmaceutical preparations.

When a product containing high contents of main components is prepared by mixing and direct tableting, tableting problems such as capping or sticking are generally caused by the properties of the main components. Fimasartan has high scattering properties due to its relatively low bulk and tapped densities and tends to agglomerate with each other. Due to its agglomerating properties, when fimasartan is mixed in a high share mixer, uniform mixing is very difficult to achieve. Moreover, there is a more than 10-fold difference in the mixing ratio of fimasartan and hydrochlorothiazide, and thus it is very difficult to prepare a granule in which the contents of two main components are uniform.

Therefore, there is a need to provide a pharmaceutical composition containing active ingredients of fimasartan and hydrochlorothiazide with excellent physical properties of granules for the preparation of tablets and high content uniformity of fimasartan and hydrochlorothiazide.

BACKGROUND ART DOCUMENT

Patent Document

Korean Patent. No. 10-1058284

DETAILED DESCRIPTION OF THE INVENTION

The present invention aims at providing a pharmaceutical composition which comprises fimasartan, a pharmaceutically acceptable salt thereof, a hydrate thereof, or a solvate thereof and hydrochlorothiazide, a pharmaceutically acceptable salt thereof, a hydrate thereof, or a solvate thereof, wherein the pharmaceutical composition exhibits high content uniformity of fimasartan and hydrochlorothiazide, which are the main components of a combination preparation, and has excellent physical properties, and a method of preparation thereof.

The present invention provides a pharmaceutical composition comprising: fimasartan, a pharmaceutically acceptable salt thereof, a hydrate thereof, or a solvate thereof; hydrochlorothiazide, a pharmaceutically acceptable salt thereof, a hydrate thereof, or a solvate thereof; and a binder having a viscosity of 20 mPa·s to 1,000 mPa·s at 25° C.

The pharmaceutical composition comprising a binder having a viscosity of 20 mPa·s to 1,000 mPa·s at room temperature of 25° C. has high content uniformity. This enables the preparation of a stable pharmaceutical composition by uniform mixing of the main components, fimasartan and hydrochlorothiazide, and the pharmaceutical composition has an excellent effect in preventing or treating cardiovascular diseases.

The binder can be starch, gelatin, glucose syrup, polyvinylpyrrolidone, acacia, polyethylene glycol 6000, methylcellulose, ethylcellulose, carboxymethylcellulose, hydroxypropyl methylcellulose, hydroxypropyl cellulose, etc, and preferably comprises at least one selected from the group consisting of hydroxypropyl cellulose, hydroxypropyl methylcellulose, and polyvinylpyrrolidone.

As used herein, the term "pharmaceutically acceptable salt" refers to a salt that is conventionally used in the pharmaceutical industry, and non-limiting examples of such salt include inorganic ion salts such as those of calcium, potassium, sodium, and magnesium, etc., inorganic acid salts such as those of hydrochloric acid, nitric acid, phosphoric acid, bromic acid, hydroiodic acid, perchloric acid, and sulfuric acid, etc., organic acid salts such as those of acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, mucic acid, pamoic acid, and pantothenic acid, etc., sulfonic acid salts such as those of methanesulfonic acid, ethanesulfonic acid, benzenesulfonic acid, p-toluenesulfonic acid, camphorsulfonic acid, or naphthalenesulfonic acid, etc., amino acid salts such as those of glycine, arginine, lysine, etc., and amine salts such as those of trimethylamine, triethylamine, ammonia, pyridine, picoline, etc.

The hydrate of fimasartan according to the present invention can be a monohydrate, dihydrate, trihydrate, tetrahydrate, pentahydrate, etc., preferably a trihydrate.

Preferably, the pharmaceutical composition comprises fimasartan potassium trihydrate and hydrochlorothiazide.

The pharmaceutical composition can be a solid preparation in the form of a tablet, pill, powder, granule, capsule, etc., preferably in the form of a tablet. The solid preparation can comprise at least one additive such as an excipient, a binder, a disintegrant, a lubricant, an adsorbent, a humectant, a coating agent, or a controlled-release additive in the composition of the present invention. Specifically, examples of the additive can comprise starch, gelatin, glucose syrup, acacia, polyethylene glycol, methylcellulose, ethylcellulose, carboxymethylcellulose sodium, avicel, carboxymethylcellulose calcium, talc, corn starch, colloidal silicon dioxide, sodium lauryl sulfate, magnesium lauryl sulfate, sodium chloride, magnesium stearate, stearic acid, glycerin, propyleneglycol, sorbitol, Eudragit, polyvinyl acetate phthalate, white beeswax, carnauba wax, paraffin, hardened vegetable oil, shellac, or zein, etc.

The tablet can be a sugar-coated tablet, coated with sugar or sugar alcohol on uncoated tablet, or a film-coated tablet, coated with an appropriate coating agent on uncoated tablet. Otherwise, the tablet can be a sustained-release tablet or enteric-coated tablet prepared by an appropriate method. Moreover, the tablet can be a multi-layered tablet prepared by compressing particulate matters of different compositions in multiple layers, or a dry-coated tablet prepared by coating an inner core tablet with an outer layer of a different composition by an appropriate method, and the tablet preferably comprises an uncoated tablet and a coating layer.

The present invention provides a method for preparing a pharmaceutical composition comprising fimasartan, a pharmaceutically acceptable salt thereof, a hydrate thereof, or a solvate thereof and hydrochlorothiazide, a pharmaceutically acceptable salt thereof, a hydrate thereof, or a solvate thereof, the method comprising the steps of:

preparing a mixture comprising fimasartan, a pharmaceutically acceptable salt thereof, a hydrate thereof, or a solvate thereof and hydrochlorothiazide, a pharmaceutically acceptable salt thereof, a hydrate thereof, or a solvate thereof;

preparing granules by mixing the mixture with a binding solution in which a binder is dissolved to exhibit a viscosity of 20 mPa·s to 1,000 mPa·s at 25° C.; and preparing an uncoated tablet containing the granules.

The pharmaceutical composition is prepared by wet granulation method, i.e. preparing a binding solution by dissolving a binder in a solvent such as purified water or ethanol, etc., and thereafter preparing the granules by dissolving active ingredients such as fimasartan, a pharmaceutically acceptable salt thereof, a hydrate thereof, or a solvate thereof and hydrochlorothiazide, a pharmaceutically acceptable salt thereof, a hydrate thereof, or a solvate thereof in the binding solution.

The binder can be starch, gelatin, glucose syrup, polyvinylpyrrolidone, acacia, polyethylene glycol 6000, methylcellulose, ethylcellulose, carboxymethylcellulose, hydroxypropyl methylcellulose, hydroxypropyl cellulose, etc. and preferably comprises at least one selected from the group consisting of hydroxypropyl cellulose, hydroxypropyl methylcellulose, and polyvinylpyrrolidone.

The binding solution having a viscosity of 20 mPa·s to 1,000 mPa·s at 25° C. can comprise hydroxypropyl cellulose, hydroxypropyl methylcellulose, or polyvinylpyrrolidone, which 3% (w/w) to 25% (w/w) at 25° C., and preferably comprises: 3% (w/w) to 15% (w/w) low viscosity hydroxypropyl cellulose (Klucel-ELF/Ashland); 3% (w/w) to 10% (w/w) high viscosity hydroxypropyl cellulose (Klucel-LF/Ashland); 3% (w/w) to 15% (w/w) hydroxypropyl methylcellulose (HPMC 2910/Methocel); or 10% (w/w) to 25% (w/w) polyvinylpyrrolidone (Kollidon 30/BASF).

In the method of preparation, when the binding solution exhibits a viscosity of 20 mPa·s to 1,000 mPa·s at room temperature of 25° C., the pharmaceutical composition has high content uniformity. This enables the preparation of a stable pharmaceutical composition by uniform mixing of fimasartan and hydrochlorothiazide, and the pharmaceutical composition has an excellent effect in preventing or treating cardiovascular diseases.

The method of preparation can further comprise the steps of:

preparing sized materials by sizing the granules;
preparing a final mixture by adding one or more additives to the sized materials; and
preparing the uncoated tablet by compressing the final mixture.

The pharmaceutical composition according to the present invention can have a relative standard deviation (RSD) 5% or less, preferably 4.0% or less, in the content uniformity test according to the content uniformity criteria described in Uniformity of Dosage Units of Korean Pharmacopoeia, 9th edition.

The pharmaceutical composition can be a solid preparation in the form of a tablet, pill, powder, granule, capsule, etc., preferably in the form of a tablet. The solid preparation can comprise at least one additive such as an excipient, a binder, a disintegrant, a lubricant, an adsorbent, a humectant, a coating agent, or a controlled-release additive in the composition of the present invention. Specifically, examples of the additive can comprise starch, gelatin, glucose syrup, acacia, polyethylene glycol, methylcellulose, ethylcellulose, carboxymethylcellulose sodium, avicel, carboxymethylcellulose calcium, talc, corn starch, colloidal silica, sodium lauryl sulfate, magnesium lauryl sulfate, sodium chloride, magnesium stearate, stearic acid, glycerin, propyleneglycol, sorbitol, Eudragit, polyvinyl acetate phthalate, white beeswax, carnauba wax, paraffin, hardened vegetable oil, shellac, or zein, etc.

The tablet can be a sugar-coated tablet, coated with a coating agent containing sugar or sugar alcohol, or a film-coated tablet, coated with an appropriate coating agent. Otherwise, the tablet can be a sustained-release tablet or enteric-coated tablet prepared by an appropriate method. Moreover, the tablet can be a multi-layered tablet prepared by compressing particulate matters of different compositions in multiple layers, or a dry-coated tablet prepared by coating an inner core tablet with an outer layer of a different composition by an appropriate method, and the tablet preferably comprises an uncoated tablet and a coating layer.

The hardness of the uncoated tablet is one suitable for compression and preferably is 7 Kp or more.

The use of the pharmaceutical composition is not particularly limited but can preferably be used for the treatment of hypertension.

The present invention provides a method for the treatment of hypertension, comprising administering a pharmaceutical composition comprising fimasartan, a pharmaceutically acceptable salt thereof, a hydrate thereof, or a solvate thereof; hydrochlorothiazide, a pharmaceutically acceptable salt thereof, a hydrate thereof, or a solvate thereof; and a binder having a viscosity of 20 mPa·s to 1,000 mPa·s at 25° C.

The composition comprising fimasartan and hydrochlorothiazide according to the present invention has an excellent effect in preventing or treating cardiovascular diseases.

Moreover, according to the present invention, when a binding solution having a viscosity of 20 mPa·s to 1,000 mPa·s is used in a combination preparation of fimasartan and hydrochlorothiazide, which tend to agglomerate and thus are not uniformly mixed and results in low content uniformity, it is possible to prepare a combination preparation of fimasartan and hydrochlorothiazide with high content uniformity and excellent physical properties such as hardness.

Hereinafter, the present invention will be described in more detail with reference to the following Examples. However, these Examples are provided only to illustrate the present invention, but the scope of the present invention is not limited thereto.

Example 1

A tablet comprising fimasartan potassium trihydrate and hydrochlorothiazide was prepared using the ingredients and contents shown in the following Table 1. 132.02 mg of fimasartan potassium trihydrate, 12.50 mg of hydrochlorothiazide, 112.48 mg of lactose hydrate, 23.50 mg of microcrystalline cellulose, and 22.50 mg of croscarmellose sodium were stirred with an agitator at 100 rpm and a chopper at 200 rpm for 2 minutes (High Share Mixer SM-5C, Sejong Pharmatech) to prepare a mixture. A binding solution prepared by dissolving 2.00 mg of low viscosity hydroxypropyl cellulose (Klucel-ELF/Ashland) in 24.0 mg of ethanol and 22.0 mg of purified water was added to the mixture, and the mixture was stirred with an agitator at 200 rpm and a chopper at 2000 rpm for 2 minutes (High Share Mixer SM-5C, Sejong Pharmatech) to prepare white granules. The granules was dried at 40° C. for 10 hours and sized with a 30-mesh sieve to prepare sized materials. Then, 22.50 mg of croscarmellose sodium and 4.50 mg of magnesium stearate were added to the sized materials to prepare a final mixture. The final mixture was compressed at a compression pressure of 20 kN to prepare an uncoated tablet comprising fimasartan potassium trihydrate and hydrochlorothiazide. The uncoated tablet was coated with HPMC-based Opadry to prepare a tablet comprising fimasartan potassium trihydrate and hydrochlorothiazide.

Example 2

A tablet comprising fimasartan potassium trihydrate and hydrochlorothiazide was prepared by substantially the same method as Example 1, except that the ingredients and contents shown in Example 2 of the following Table 1 were used.

Example 3

A tablet comprising fimasartan potassium trihydrate and hydrochlorothiazide was prepared by substantially the same method as Example 1, except that the ingredients and contents shown in Example 3 of the following Table 1 were used.

TABLE 1

|  | Example 1 | Example 2 | Example 3 |
| --- | --- | --- | --- |
| Mixing part | | | |
| Fimasartan potassium trihydrate | 132.02 mg | 132.02 mg | 132.02 mg |
| Hydrochlorothiazide | 12.50 mg | 12.50 mg | 12.50 mg |
| Lactose hydrate | 112.48 mg | 110.48 mg | 108.48 mg |
| Microcrystalline cellulose | 23.50 mg | 23.50 mg | 23.50 mg |
| Croscarmellose sodium | 22.50 mg | 22.50 mg | 22.50 mg |
| Binding solution part | | | |
| Low viscosity hydroxypropyl cellulose (Klucel-ELF/Ashland) | 2.00 mg | 4.00 mg | 6.00 mg |
| Ethanol | 24.0 mg | 24.0 mg | 24.0 mg |
| Purified water | 22.0 mg | 22.0 mg | 22.0 mg |
| Final mixing part | | | |
| Croscarmellose sodium | 22.50 mg | 22.50 mg | 22.50 mg |
| Magnesium stearate | 4.50 mg | 4.50 mg | 4.50 mg |

Example 4

A tablet comprising fimasartan potassium trihydrate and hydrochlorothiazide was prepared by substantially the same method as Example 1, except that the ingredients and contents shown in Example 4 of the following Table 2 were used.

Example 5

A tablet comprising fimasartan potassium trihydrate and hydrochlorothiazide was prepared by substantially the same method as Example 1, except that the ingredients and contents shown in Example 5 of the following Table 2 were used.

TABLE 2

|  | Example 4 | Example 5 |
| --- | --- | --- |
| Mixing part | | |
| Fimasartan potassium trihydrate | 132.02 mg | 132.02 mg |
| Hydrochlorothiazide | 12.50 mg | 12.50 mg |
| Lactose hydrate | 112.48 mg | 110.48 mg |
| Microcrystalline cellulose | 23.50 mg | 23.50 mg |
| Croscarmellose sodium | 22.50 mg | 22.50 mg |
| Binding solution part | | |
| High viscosity hydroxypropyl cellulose (Klucel-LF/Ashland) | 2.00 mg | 4.00 mg |
| Ethanol | 24.0 mg | 24.0 mg |
| Purified water | 22.0 mg | 22.0 mg |
| Final mixing part | | |
| Croscarmellose sodium | 22.50 mg | 22.50 mg |
| Magnesium stearate | 4.50 mg | 4.50 mg |

Example 6

A tablet comprising fimasartan potassium trihydrate and hydrochlorothiazide was prepared by substantially the same method as Example 1, except that the ingredients and contents shown in Example 6 of the following Table 3 were used.

Example 7

A tablet comprising fimasartan potassium trihydrate and hydrochlorothiazide was prepared by substantially the same method as Example 1, except that the ingredients and contents shown in Example 7 of the following Table 3 were used.

Example 8

A tablet comprising fimasartan potassium trihydrate and hydrochlorothiazide was prepared by substantially the same method as Example 1, except that the ingredients and contents shown in Example 8 of the following Table 3 were used.

TABLE 3

|  | Example 6 | Example 7 | Example 8 |
| --- | --- | --- | --- |
| Mixing part | | | |
| Fimasartan potassium trihydrate | 132.02 mg | 132.02 mg | 132.02 mg |
| Hydrochlorothiazide | 12.50 mg | 12.50 mg | 12.50 mg |
| Lactose hydrate | 112.48 mg | 110.48 mg | 108.48 mg |
| Microcrystalline cellulose | 23.50 mg | 23.50 mg | 23.50 mg |
| Croscarmellose sodium | 22.50 mg | 22.50 mg | 22.50 mg |
| Binding solution part | | | |
| Hydroxypropyl methylcellulose (Methocel E5/Dow Chemical) | 2.00 mg | 4.00 mg | 6.00 mg |

TABLE 3-continued

|  | Example 6 | Example 7 | Example 8 |
|---|---|---|---|
| Ethanol | 24.0 mg | 24.0 mg | 24.0 mg |
| Purified water | 22.0 mg | 22.0 mg | 22.0 mg |
| Final mixing part | | | |
| Croscarmellose sodium | 22.50 mg | 22.50 mg | 22.50 mg |
| Magnesium stearate | 4.50 mg | 4.50 mg | 4.50 mg |

Example 9

A tablet comprising fimasartan potassium trihydrate and hydrochlorothiazide was prepared by substantially the same method as Example 1, except that the ingredients and contents shown in Example 9 of the following Table 4 were used.

Example 10

A tablet comprising fimasartan potassium trihydrate and hydrochlorothiazide was prepared by substantially the same method as Example 1, except that the ingredients and contents shown in Example 10 of the following Table 4 were used.

Example 11

A tablet comprising fimasartan potassium trihydrate and hydrochlorothiazide was prepared by substantially the same method as Example 1, except that the ingredients and contents shown in Example 11 of the following Table 4 were used.

TABLE 4

|  | Example 9 | Example 10 | Example 11 |
|---|---|---|---|
| Mixing part | | | |
| Fimasartan potassium trihydrate | 132.02 mg | 132.02 mg | 132.02 mg |
| Hydrochlorothiazide | 12.50 mg | 12.50 mg | 12.50 mg |
| Lactose hydrate | 108.48 mg | 106.48 mg | 104.48 mg |
| Microcrystalline cellulose | 23.50 mg | 23.50 mg | 23.50 mg |
| Croscarmellose sodium | 22.50 mg | 22.50 mg | 22.50 mg |
| Binding solution part | | | |
| Polyvinylpyrrolidone (Kollidon 30/BASF) | 6.00 mg | 8.00 mg | 10.00 mg |
| Ethanol | 24.0 mg | 24.0 mg | 24.0 mg |
| Purified water | 22.0 mg | 22.0 mg | 22.0 mg |
| Final mixing part | | | |
| Croscarmellose sodium | 22.50 mg | 22.50 mg | 22.50 mg |
| Magnesium stearate | 4.50 mg | 4.50 mg | 4.50 mg |

Comparative Example 1

A tablet comprising fimasartan potassium trihydrate and hydrochlorothiazide was prepared by substantially the same method as Example 1, except that the ingredients and contents shown in Comparative Example 1 of the following Table 5 were used.

Comparative Example 2

A tablet comprising fimasartan potassium trihydrate and hydrochlorothiazide was prepared by substantially the same method as Example 1, except that the ingredients and contents shown in Comparative Example 2 of the following Table 5 were used.

Comparative Example 3

A tablet comprising fimasartan potassium trihydrate and hydrochlorothiazide was prepared by substantially the same method as Example 1, except that the ingredients and contents shown in Comparative Example 3 of the following Table 5 were used.

TABLE 5

|  | Comparative Example 1 | Comparative Example 2 | Comparative Example 3 |
|---|---|---|---|
| Mixing part | | | |
| Fimasartan potassium trihydrate | 132.02 mg | 132.02 mg | 132.02 mg |
| Hydrochlorothiazide | 12.50 mg | 12.50 mg | 12.50 mg |
| Lactose hydrate | 106.48 mg | 104.48 mg | 108.48 mg |
| Microcrystalline cellulose | 23.50 mg | 23.50 mg | 23.50 mg |
| Croscarmellose sodium | 22.50 mg | 22.50 mg | 22.50 mg |
| Binding solution part | | | |
| Low viscosity hydroxypropyl cellulose (Klucel-ELF/Ashland) | 8.00 mg | 10.00 mg | — |
| High viscosity hydroxypropyl cellulose (Klucel-LF/Ashland) | — | — | 6.00 mg |
| Ethanol | 24.0 mg | 24.0 mg | 24.0 mg |
| Purified water | 22.0 mg | 22.0 mg | 22.0 mg |
| Final mixing part | | | |
| Croscarmellose sodium | 22.50 mg | 22.50 mg | 22.50 mg |
| Magnesium stearate | 4.50 mg | 4.50 mg | 4.50 mg |

Comparative Example 4

A tablet comprising fimasartan potassium trihydrate and hydrochlorothiazide was prepared by substantially the same method as Example 1, except that the ingredients and contents shown in Comparative Example 4 of the following Table 6 were used.

Comparative Example 5

A tablet comprising fimasartan potassium trihydrate and hydrochlorothiazide was prepared by substantially the same method as Example 1, except that the ingredients and contents shown in Comparative Example 5 of the following Table 6 were used.

Comparative Example 6

A tablet comprising fimasartan potassium trihydrate and hydrochlorothiazide was prepared by substantially the same method as Example 1, except that the ingredients and contents shown in Comparative Example 6 of the following Table 6 were used.

TABLE 6

|  | Comparative Example 4 | Comparative Example 5 | Comparative Example 6 |
|---|---|---|---|
| Mixing part | | | |
| Fimasartan potassium trihydrate | 132.02 mg | 132.02 mg | 132.02 mg |

TABLE 6-continued

|  | Comparative Example 4 | Comparative Example 5 | Comparative Example 6 |
|---|---|---|---|
| Hydrochlorothiazide | 12.50 mg | 12.50 mg | 12.50 mg |
| Lactose hydrate | 106.48 mg | 112.48 mg | 110.48 mg |
| Microcrystalline cellulose | 23.50 mg | 23.50 mg | 23.50 mg |
| Croscarmellose sodium | 22.50 mg | 22.50 mg | 22.50 mg |
| Binding solution part | | | |
| Hydroxypropyl methylcellulose (HPMC 2910/Methocel) | 8.00 mg | — | — |
| Polyvinylpyrrolidone (Kollidon 30/BASF) | — | 2.00 mg | 4.00 mg |
| Ethanol | 24.0 mg | 24.0 mg | 24.0 mg |
| Purified water | 22.0 mg | 22.0 mg | 22.0 mg |
| Final mixing part | | | |
| Croscarmellose sodium | 22.50 mg | 22.50 mg | 22.50 mg |
| Magnesium stearate | 4.50 mg | 4.50 mg | 4.50 mg |

Comparative Example 7

A tablet comprising fimasartan potassium trihydrate and hydrochlorothiazide was prepared by substantially the same method as Example 1, except that the ingredients and contents shown in Comparative Example 7 of the following Table 7 were used.

Comparative Example 8

A tablet comprising fimasartan potassium trihydrate and hydrochlorothiazide was prepared by substantially the same method as Example 1, except that the ingredients and contents shown in Comparative Example 8 of the following Table 7 were used.

Comparative Example 9

A tablet comprising fimasartan potassium trihydrate and hydrochlorothiazide was prepared by substantially the same method as Example 1, except that the ingredients and contents shown in Comparative Example 9 of the following Table 7 were used.

TABLE 7

|  | Comparative Example 7 | Comparative Example 8 | Comparative Example 9 |
|---|---|---|---|
| Mixing part | | | |
| Fimasartan potassium trihydrate | 132.02 mg | 132.02 mg | 132.02 mg |
| Hydrochlorothiazide | 12.50 mg | 12.50 mg | 12.50 mg |
| Lactose hydrate | 106.48 mg | 112.48 mg | 110.48 mg |
| Microcrystalline cellulose | 23.50 mg | 23.50 mg | 23.50 mg |
| Croscarmellose sodium | 22.50 mg | 22.50 mg | 22.50 mg |
| Binding solution part | | | |
| High viscosity hydroxypropyl cellulose (Klucel-LF/Ashland) | 8.00 mg | 10.00 mg | — |
| Hydroxypropyl methylcellulose (HPMC 2910/Methocel) | — | — | 10.00 mg |
| Ethanol | 24.0 mg | 24.0 mg | 24.0 mg |
| Purified water | 22.0 mg | 22.0 mg | 22.0 mg |
| Final mixing part | | | |
| Croscarmellose sodium | 22.50 mg | 22.50 mg | 22.50 mg |
| Magnesium stearate | 4.50 mg | 4.50 mg | 4.50 mg |

Experimental Example 1

Viscosity Test of Bindings Solutions Depending on Type and Concentration of Binders The viscosities of the binding solutions used in Examples 1 to 11 and Comparative Example 1 to 9 were measured using a viscometer (Fungilab/Visco Basic-L) at room temperature of 25° C. The results of the viscosity test are shown in Table 8:

TABLE 8

|  | Ex. 1 | Ex. 2 | Ex. 3 | Ex. 4 | Ex. 5 | Ex. 6 | Ex. 7 |
|---|---|---|---|---|---|---|---|
| Viscosity (mPa · s) | 20 | 140 | 480 | 80 | 640 | 30 | 230 |

|  | Ex. 8 | Ex. 9 | Ex. 10 | Ex. 11 | Comp. Ex. 1 | Comp. Ex. 2 | Comp. Ex. 3 |
|---|---|---|---|---|---|---|---|
| Viscosity (mPa · s) | 650 | 26 | 31 | 39 | 1110 | 2210 | 1930 |

|  | Comp. Ex. 4 | Comp. Ex. 5 | Comp. Ex. 6 | Comp. Ex. 7 | Comp. Ex. 8 | Comp. Ex. 9 |  |
|---|---|---|---|---|---|---|---|
| Viscosity (mPa · s) | 1640 | 7 | 12 | — | — | — |  |

In the above table 8, the preparation of the binding solution was stopped because excess load was applied to the mixer due to high viscosity when the concentration of high viscosity hydroxypropyl cellulose (Klucel-LF/Ashland) was 17.4% (Comparative Examples 7 and 8) that was higher than the concentration of the binding solution, 13.0%, and the preparation of the binding solution was also stopped by the same problem when the concentration of hydroxypropyl methylcellulose was 21.7% (Comparative Example 9). According to the test results, the binding solutions that were not prepared in Comparative Examples 7 to 9 were not used in the next experiment.

Experimental Example 2

Content Uniformity Test of Fimasartan Potassium Trihydrate and Hydrochlorothiazide The content uniformity test of fimasartan potassium trihydrate and hydrochlorothiazide was performed on the samples collected from a total of 10 portions of the final mixtures by HPLC. The analysis conditions of HPLC are shown in Table 9, and the preparation process of the standard solution and the test solution are shown in Table 10. The results of the content uniformity test are shown in Table 11, in which F represents fimasartan potassium trihydrate and H represents hydrochlorothiazide.

TABLE 9

| Column | Xterra C18 (5 microns, 250 * 4.6 mm) |
|---|---|
| Device | Detection 260 nm |
| Diluent | Temperature 40° C. |
| Buffer | Run time 16 min |
| Mobile phase | Injection 20 uL |
| | Flow rate 1.0 mL/min |
| | Sample Temp. 25° C. |
| | MeOH |
| | 0.01M phosphate buffer (pH 2.5) |
| | Buffer:Acetonitrile = 60:40 |

TABLE 10

| Preparation of standard solution | Preparation of test solution |
|---|---|
| A. Taking an amount corresponding to 66.0 mg of fimasartan potassium trihydrate | Taking an amount corresponding to one tablet |
| ↓← Diluent 50 mL v/f | ↓← Purified water 10 mL Sonication for 30 sec. |
| B. Taking an amount corresponding to 12.5 mg of hydrochlorothiazide | ↓← Diluent 60 mL Sonication for 20 min. |
| ↓← Diluent 100 mL v/f | ↓← Diluent 100 mL v/f |
| Taking each 5 mL of A and B | Taking 5 mL |
| ↓← Mobile phase 200 mL v/f | ↓← Mobile phase 200 mL v/f |

As can be seen from the above Table 11, in Examples 1 to 11 and Comparative Examples 5 and 6, where binding solutions with viscosities less than 1,000 mPa·s were used, the relative standard deviations (RSDs) were 4.0% or less, indicating high content uniformity. However, in Comparative Examples 1 to 4 where binding solutions with viscosities of 1,000 mPa·s or more were used, the relative standard deviations (RSDs) were significantly increased to 9.21 to 15.87%, indicating low content uniformity. According to the test results, it could be found that the content uniformity of the final mixture of fimasartan potassium trihydrate and hydrochlorothiazide of the present invention is high when a binding solution with a viscosity in less than 1,000 mPa·s is used. Moreover, it can be seen that the binding solution preferably contains 4.3% (w/w) to 13.0% (w/w) low viscosity hydroxypropyl cellulose (Klucel-ELF/Ashland); 4.3% (w/w) to 8.7% (w/w) high viscosity hydroxypropyl cellulose (Klucel-LF/Ashland); 4.3% (w/w) to 13.0% (w/w) hydroxypropyl methylcellulose (HPMC 2910/Methocel); or 13.0% (w/w) to 21.7% (w/w) polyvinylpyrrolidone (Kollidon 30/BASF) in a solvent at 25° C.

Experimental Example 3

Hardness Test of Uncoated Tablets Comprising Fimasartan Potassium Trihydrate and Hydrochlorothiazide The hardness test for coating an uncoated tablet comprising fimasartan potassium trihydrate and hydrochlorothiazide was performed by compression at a pressure of 20 kN. In order to coat the uncoated tablet comprising fimasartan potassium trihydrate and hydrochlorothiazide, the uncoated tablet should have a minimum hardness of 7 to 8 Kp, and when the hardness is below 7 Kp, the tablet can be broken or worn during the coating process, which makes it impossible to obtain a final product of good quality. The results of the hardness test are shown in Table 12.

TABLE 12

| | Sample | | | | | |
|---|---|---|---|---|---|---|
| | Ex. 1 | Ex. 2 | Ex. 3 | Ex. 4 | Ex. 5 | Ex. 6 |
| Average hardness (Kp) | 7.1 | 8.6 | 10.7 | 8.1 | 11.9 | 7.5 |

TABLE 11

| | Ex. 1 | | Ex. 2 | | Ex. 3 | | Ex. 4 | | Ex. 5 | | Ex. 6 | |
|---|---|---|---|---|---|---|---|---|---|---|---|---|
| | F (%) | H (%) | F (%) | H (%) | F (%) | H (%) | F (%) | H (%) | F (%) | H (%) | F (%) | H (%) |
| Mean | 97.2 | 96.9 | 100.3 | 97.9 | 99.5 | 99.1 | 98.6 | 97.2 | 99.2 | 98.6 | 99.6 | 98.1 |
| RSD | 2.93 | 3.43 | 3.17 | 3.04 | 1.76 | 1.34 | 2.29 | 2.36 | 3.18 | 3.05 | 2.49 | 2.42 |

| | Ex. 7 | | Ex. 8 | | Ex. 9 | | Ex. 10 | | Ex. 11 | |
|---|---|---|---|---|---|---|---|---|---|---|
| | F (%) | H (%) | F (%) | H (%) | F (%) | H (%) | F (%) | H (%) | F (%) | H (%) |
| Mean | 98.3 | 97.4 | 99.1 | 97.7 | 100.1 | 98.7 | 98.1 | 97.8 | 99.4 | 98.3 |
| RSD | 3.03 | 2.96 | 2.24 | 2.01 | 3.14 | 2.76 | 2.34 | 2.87 | 3.34 | 3.07 |

| | Comp. Ex. 1 | | Comp. Ex. 2 | | Comp. Ex. 3 | | Comp. Ex. 4 | | Comp. Ex. 5 | | Comp. Ex. 6 | |
|---|---|---|---|---|---|---|---|---|---|---|---|---|
| | F (%) | H (%) | F (%) | H (%) | F (%) | H (%) | F (%) | H (%) | F (%) | H (%) | F (%) | H (%) |
| Mean | 97.1 | 95.4 | 97.4 | 96.3 | 98.3 | 97.5 | 109.4 | 98.6 | 99.9 | 98.8 | 98.9 | 98.3 |
| RSD | 9.21 | 9.47 | 10.58 | 10.55 | 15.87 | 14.95 | 12.02 | 13.53 | 3.35 | 3.25 | 3.17 | 3.38 |

TABLE 12-continued

| | Sample | | | | |
|---|---|---|---|---|---|
| | Ex. 7 | Ex. 8 | Ex. 9 | Ex. 10 | Ex. 11 |
| Average hardness (Kp) | 8.6 | 11.7 | 7.2 | 7.1 | 7.6 |

| | Sample | | | | | |
|---|---|---|---|---|---|---|
| | Comp. Ex. 1 | Comp. Ex. 2 | Comp. Ex. 3 | Comp. Ex. 4 | Comp. Ex. 5 | Comp. Ex. 6 |
| Average hardness (Kp) | 12.3 | 13.7 | 13.5 | 13.3 | 3.4 | 4.7 |

As can be seen from the above Table 12, it was confirmed that in Comparative Examples 5 and 6 where binding solutions with viscosities in less than 20 mPa·s were used, the hardness was measured as 3.4 Kp and 4.7 Kp, respectively, indicating that the hardness is not suitable for the coating process. According to the test results, it was found that when a binding solution with a viscosity of 20 mPa·s or more was used to coat the uncoated tablet comprising fimasartan potassium trihydrate and hydrochlorothiazide, it is possible to produce a combination preparation having high hardness of 7 Kp or more.

As described above, the composition comprising fimasartan and hydrochlorothiazide according to the present invention has an excellent effect in preventing or treating cardiovascular diseases.

Moreover, according to the present invention, when a binding solution having a viscosity of 20 mPa·s to 1,000 mPa·s is used in a preparation with combined fimasartan and hydrochlorothiazide, which tend to agglomerate and thus are not uniformly mixed and resulting low content uniformity, it is possible to prepare a preparation with combined fimasartan and hydrochlorothiazide with high content uniformity and excellent, physical properties such as hardness.

The invention claimed is:

1. A pharmaceutical composition comprising:
    fimasartan, a pharmaceutically acceptable salt thereof, a hydrate thereof, or a solvate thereof;
    hydrochlorothiazide, a pharmaceutically acceptable salt thereof, a hydrate thereof, or a solvate thereof; and
    a binder exhibiting a viscosity of 20 mPa·s to 1,000 mP·s at 25° C.;
    wherein the pharmaceutical composition is in the form of a tablet; and
    wherein the pharmaceutical composition has high content uniformity.

2. The pharmaceutical composition of claim 1, wherein the binder comprises at least one selected from the group consisting of hydroxypropyl cellulose, hydroxypropyl methylcellulose, and polyvinylpyrrolidone.

3. The pharmaceutical composition of claim 1, wherein the pharmaceutical composition has a relative standard deviation (RSD) of 4.0% or less in content uniformity test.

4. The pharmaceutical composition of claim 1, wherein the tablet comprises an uncoated tablet and a coating layer.

5. The pharmaceutical composition of claim 4, wherein the uncoated tablet has a hardness of 7 Kp or more.

6. The pharmaceutical composition of claim 1, wherein the pharmaceutical composition is used for the treatment of hypertension.

7. A method of preparing the pharmaceutical composition of claim 1 comprising the steps of:
    preparing a mixture comprising fimasartan, a pharmaceutically acceptable salt thereof, a hydrate thereof, or a solvate thereof and hydrochlorothiazide, a pharmaceutically acceptable salt thereof, a hydrate thereof, or a solvate thereof;
    preparing granules by mixing the mixture with a binding solution in which a binder is dissolved to exhibit a viscosity of 20 mPa·s to 1,000 mPa·s at 25° C.; and
    preparing an uncoated tablet containing the granules.

8. The method of claim 7, further comprising the steps of:
    preparing sized materials by sizing the granules;
    preparing a final mixture by adding one or more additives to the sized materials; and
    preparing the uncoated tablet by compressing the final mixture.

9. The method of claim 7, wherein the binder comprises at least one selected from the group consisting of hydroxypropyl cellulose, hydroxypropyl methylcellulose, and polyvinylpyrrolidone.

10. The method of claim 7, wherein the pharmaceutical composition has a relative standard deviation (RSD) of 4.0% or less in content uniformity test.

11. The method of claim 7, wherein the uncoated tablet has a hardness of 7 Kp or more.

12. The method of claim 7, wherein the pharmaceutical composition is used for the treatment of hypertension.

13. A tablet prepared by the method of claim 7.
14. A tablet prepared by the method of claim 8.
15. A tablet prepared by the method of claim 9.
16. A tablet prepared by the method of claim 10.
17. A tablet prepared by the method of claim 11.
18. A tablet prepared by the method of claim 12.

* * * * *